United States Patent [19]
Zelman

[11] Patent Number: 5,571,124
[45] Date of Patent: Nov. 5, 1996

[54] APPARATUS AND METHOD FOR PERFORMING SURGERY ON THE CORNEA OF AN EYE

[76] Inventor: Jerry Zelman, 31 The Glen, Glen Head, N.Y. 11545

[21] Appl. No.: 421,316

[22] Filed: Apr. 13, 1995

[51] Int. Cl.⁶ .................................................. A61F 9/00
[52] U.S. Cl. .......................................... 606/166; 606/167
[58] Field of Search ................................... 606/166, 167, 606/170, 172

[56] References Cited

U.S. PATENT DOCUMENTS

| | | |
|---|---|---|
| 3,798,688 | 3/1974 | Wasson . |
| 4,552,146 | 11/1985 | Jensen et al. . |
| 4,602,630 | 7/1986 | Anis . |
| 4,672,965 | 6/1987 | Baum . |
| 4,739,761 | 4/1988 | Grandon ................................. 606/166 |
| 4,759,363 | 7/1988 | Jensen . |
| 4,884,569 | 12/1989 | Fedrov et al. . |
| 5,201,747 | 4/1993 | Mastel ..................................... 606/167 |
| 5,203,865 | 4/1993 | Siepser . |
| 5,222,967 | 6/1993 | Casebeer et al. . |
| 5,336,236 | 8/1994 | Nevyas-Wallace ..................... 606/166 |
| 5,423,840 | 6/1995 | Casebeer et al. ........................ 606/166 |

*Primary Examiner*—Michael Powell Buiz
*Assistant Examiner*—Mark S. Leonardo
*Attorney, Agent, or Firm*—Sterne, Kessler, Goldstein & Fox, P.L.L.C.

[57] ABSTRACT

The present invention includes a cutting blade for performing eye surgery. The cutting blade has a dull distal edge. The sides of the cutting blade have edges, at least a portion of which are sharp. The distal edge extends between the first and second edges in a single plane thereby defining a single line from the first edge to the second edge. The cutting blade may be mounted on a handpiece such that the dull distal edge is disposed substantially perpendicular to a longitudinal axis of the handle. The handpiece may include a micrometer control for controlling the amount of the blade which extends from the handpiece. In one embodiment the handpiece is weighted to assist the surgeon in deepening the incision. In addition, transparent footplates may be mounted on the handpiece. In use, the blade of the present invention may be used alone or in combination with conventional surgical blades. With the use of the dull distal edge and the sharp edges of the blade of the present invention, an incision made in the cornea of an eye may be evened-out at its bottom and deepened across almost its entire length to almost 100% of the cornea thickness without perforating the cornea. In one embodiment, prior to cutting, a marking device of the present invention may be used to mark a pattern of incisions on the cornea of the eye. The marking device of the present invention includes concentric rings attached to each other by radially extending supports and the combination is attached to an end of a handle. The two concentric rings define the maximum length of the radial incisions.

19 Claims, 5 Drawing Sheets

APPARATUS AND METHOD FOR PERFORMING SURGERY ON THE CORNEA OF AN EYE

BACKGROUND OF THE INVENTION

1. Field of the Invention

This invention relates to a blade for use in eye surgery and a method for performing a surgical procedure on a cornea of the eye. More particularly, this invention relates to a marking device for marking the cuts to be made in the eye, a blade with a planar, dull distal edge and a method for deepening incisions in the cornea of the eye using the blade of the present invention.

2. Description of Related Art

Refractive errors, such as myopia (nearsightedness) and astigmatism, are commonly corrected with eye glasses or contact lenses. However, radial and astigmatic keratotomy offer an alternative method of vision correction for many people with refractive errors who are not satisfied with glasses or contacts. Performed since the early 1970s, radial keratotomy (RK) has generally produced good results in the permanent correction of myopia. A modification of the RK procedure, astigmatic keratotomy (AK), generally provides permanent correction of astigmatism.

A refractive error is a defect in the way light passes through the eye. In normal vision, light enters the eye through the cornea and is focused at a single point on the retina at the back of the eye. With a refractive error, light rays do not refract (bend) properly to achieve a single focus point. Instead, light rays focus in front of the retina, behind the retina, or at two different points. Refractive errors usually result from a defect in the length of the eye or shape of the cornea.

Myopia is a condition in which close objects are seen clearly but distant objects appear blurred. Nearsightedness results from a lengthened eyeball (which is more oval than round) or a cornea that is curved too steeply. The increased length of the eye or the steep curve of the cornea causes the light rays to be focused in front of the retina.

Astigmatism, a condition in which objects at all distances appear somewhat indistinct and distorted rather than sharp and clear, is caused by a misshaped cornea. Because the curve of the cornea is uneven or warped instead of an even curve, the light rays are not refracted equally in all directions. As a result, a single focus point on the retina is not achieved and distorted vision occurs.

Keratotomy is a generally effective surgical technique used to correct or reduce nearsightedness and astigmatism. The procedure involves the strategic placement of tiny incisions on the surface of the cornea. Radial and astigmatic keratotomy alter the shape of the cornea so that light rays focus precisely on the retina.

To correct nearsightedness, the surgeon makes radial incisions in the outer surface of the cornea, while looking through a high power surgical microscope. The incisions do not go through the central cornea. A clear ring is left centrally as the "optical zone." The incisions are made in a pattern similar to the spokes on a wheel, with the central optical zone on the hub.

AK is very similar to RK. However, the pattern of the incisions is modified to achieve the astigmatic correction. Horizontal or curvilinear incisions are used to correct astigmatism. A combination of both radial and astigmatic keratotomy can be used in a single procedure in patients with both myopia and astigmatism.

Before surgery, thorough testing is performed to determine the amount of myopia and/or astigmatism and the diameter, thickness, curvature and health of the cornea. From this information, a surgical plan is developed. The exact number, depth, length and location of the incisions must be carefully planned to achieve the desired flattening and optical correction.

The precise incisions on the outer portion of the cornea allow the center of the cornea to flatten. When the incisions heal, the cornea has a different shape, a flatter center. The flattening of the cornea moves the focal point closer to the correct position on the retina, similar to the way glasses and contact lenses correct the path of light rays as they enter the eye.

Exact incisions having a precise depth are important so that the correction of curvature of the cornea is not too great or not great enough. In RK or AK surgery, the amount of eyesight correction achieved is directly related not only to the length of the incisions but also to the depth of the incisions made by the surgeon. However, as with any surgical procedure, complications, such as perforation of the cornea, occur. It is also possible that no visual improvement may result or vision may improve only temporarily so that a second procedure may be required.

To perform keratotomy, a knife blade is held by a handle which normally includes a pair of footplates positioned on either side of the blade, and are designed to slide along the outer surface of the cornea. The location of the footplates relative to the tip or point of the blade can be adjusted by a micrometer setting to control the depth of the cut.

Since keratotomy involves cutting the cornea of a human eye, great care must be taken to make sure that the cuts are precise and at the depth necessary to provide for the indicated correction. Consistent results are difficult to achieve.

At this time, there are instruments that exist that fairly accurately measure the length and number of corneal incisions. There are also instruments that measure the thickness of the cornea. These instruments are called pachymeters. However, there is no device or method currently available for ensuring the precise depth of an incision as it is made by the surgeon. This problem is made even more difficult because the thickness of the cornea changes radially from the central portion of the cornea to the peripheral portion of the cornea. The ability to ensure the exact depth of the incision is critical because an operation on the cornea is only successful if the incisions are cut into 90% or more of the depth or thickness of the cornea, but less than 100% of the thickness of the cornea for the entire length of the incision. Obviously, if the incision is too deep, the cornea may be perforated which can lead to severe complications. In the alternative, if the incisions are too shallow, the net effect of the surgery fails to correct the problem.

Presently, micrometer knives with diamond cutting blades are used to cut incisions in the cornea. These blades are very sharp along the edges and merge at their tip to form a sharp point. Since the exact depth of the cut cannot be positively known or observed during surgery, even if the surgeon is highly skilled, the depth of the cut may be too shallow or too deep which in either case results in an unsuccessful operation. Accordingly, cuts are normally made conservatively because the knife if extremely sharp and many surgeons tend to be over-cautious, especially, when the knife is close to the optical zone. As a result, when the incisions in the cornea are not deep and precise enough, then the problem which has been known to occur is an undercorrection of the myopia, for example.

Moreover, when the tip of this diamond blade approaches cutting 90% of the thickness of the cornea, the risk of perforating the cornea is high due to the sharpness of the blade tip. With such a sharp point it is easy to prick completely through the cornea. The risk of perforating the cornea further increases when attempts are made to cut the incision beyond 90% of the thickness of the cornea. As a result, it is difficult, if not impossible, to obtain an incision that extends into 90% or more of the thickness of the cornea, while, at the same time, avoiding perforation of the cornea.

In addition, with this sharp pointed tip blade it is difficult for a surgeon to control the consistent depth of the blade even when footplates are used. In particular, since the tip of the blade terminates in a point, it is easy for the tip to penetrate further into the depth of the cornea with an unintentional slight increase in pressure by the surgeon. Moreover, it is difficult for a surgeon to obtain a smooth even cut bottom. Because the surgeon is moving a pointed tip along the cornea, it is likely that the tip of the blade in combination with an unsteady surgeon's hand will cut an incision with an uneven bottom. When the bottom of the incision becomes unsmooth or wavy the success of the surgery is compromised.

Another problem arises when the knife blade was not properly set during cutting of the incision and the incision is cut too shallow, for example. In such case, it is difficult to retrace the cut at the proper blade setting without straying from the exact path of the initial cut with the sharp diamond blade. Additionally, it is difficult to enhance or deepen an existing incision without the fear of perforating the cornea.

Moreover, the problem of glare exists in this type of surgery. In particular, the incision made in the cornea of the eye can reflect light causing glare. When incisions are cut too close to the optical zone of the eye, the glare caused by the incision frequently reflects into the optical zone of the eye. Glare can compromise the patient's vision as well as be a nuisance to the patient.

Accordingly, the need exists for an apparatus and a method for cutting and ensuring the precise depth of an incision being made into the thickness of the cornea, as well as, a constant cut into 90% or more of the cornea along almost the entire length of the incision. More particularly, what is needed is an apparatus and method for reliably and safely cutting or enhancing incisions in the cornea at a depth of 90% or more of the depth of the cornea without the risk of perforating the cornea.

SUMMARY OF THE INVENTION

Accordingly, it is an object of the present invention to provide an apparatus that will accurately and consistently cut incisions of a measured depth into the cornea.

Another object of the invention is to provide an apparatus that is capable of reliably cutting incisions into the cornea at a depth of 90% and more of the thickness of the cornea while avoiding perforation of the cornea.

Another object of the invention is to provide a blade that can be guided along a bottom of the incision.

Another object of the invention is to provide a blade that eliminates unevenness at the bottom of the incision.

Another object of the invention is to provide a corneal marker to mark the length and/or placement of the incisions on the cornea of an eye.

Another object of the invention is to reduce glare problems associated with keratotomy.

Another object of the invention is to provide a device that can cut precise corneal incisions without the surgeon having to apply excessive pressure to the device.

Another object of the invention is to provide the surgeon with improved visual access to a preexisting incision when deepening the preexisting incision.

The present invention relates to a surgical instrument having a handle with a longitudinal axis. A blade having a shank attached to the handle includes a first edge which is sharpened to form a first cutting edge and a second edge disposed on a side of the blade which is opposite to the first edge is also sharpened to form a second cutting edge. A third edge disposed on a side of the blade which is opposite to the shank and which is dull. The third edge extends between the first edge and the second edge in a single plane which is substantially perpendicular to the longitudinal axis of the handle so that the third edge defines a single straight line.

In use, the blade of the present invention may be used to perform a surgical procedure on the cornea of an eye. The surgical procedure using the handpiece and the blade of the present invention may be used in cooperation with conventional pachymetry such the thickness of the cornea can be measured. Then a blade of the present invention that has a sharp edge and a dull edge is inserted into the cornea of the eye. An incision is created in the cornea of the eye which is almost the entire thickness of the cornea without perforating the cornea by moving the sharp edge of the blade along the cornea. The dull edge of the blade is moved along the descements membrane of the cornea while creating the incision.

The surgical procedure using the handpiece and the blade of the present invention also may be used in cooperation with a conventional surgical knife having a blade with a sharp tip and one or more sharp edges. This type of method for performing a surgical procedure on the cornea of an eye includes measuring the cornea and then cutting an initial incision in the cornea at a first depth that is equal to or less than approximately 90% of the thickness of the central cornea using a first blade having at least one sharp edge and a pointed tip. Then the incision is enhanced by disposing a second blade set at a second depth, which is equal to the depth of the peripheral cornea. The second depth is usually 100 microns deeper than the first depth set for the initial incision. The second blade has a sharp edge and a dull edge in the incision and moving the dull edge of the second blade along the base of the initial incision and cutting the cornea with the sharp edge to enhance the depth of the incision. The incision is deepened to almost the entire thickness of the cornea consistently and evenly across almost an entire length of the incision without perforating the cornea.

A marking device of the present invention also may be used to mark the cornea of the eye after measuring the cornea. In use, the marking device is constructed such that the surface of the cornea is marked with a first mark having a first diameter and a second mark concentric to first mark having a second diameter greater than the first diameter. In one embodiment, the distance between the first and second marks defines a maximum length of an incision to be cut in the cornea to perform a mini RK surgery, which is possible with the present invention. In another embodiment using this marking device, the initial incision is cut extending between an outer periphery of the eye and the first mark using the first blade, and a portion of the initial incision extending between the outer periphery of the eye and the second mark is enhanced using the second blade, which is the blade of the present invention.

In another aspect of the invention, a kit is provided for use in a surgical procedure on a cornea of an eye. The kit includes a marking device and a surgical instrument. The marking device is for marking the cornea of the eye with a pattern of marks. The marking device includes a handle, an outer marker attached to the handle having a first diameter and a central marker attached radially inward from and concentric to the outer marker by radially extending supports. The surgical instrument includes a handle having a longitudinal axis and a blade having a shank attached to said handle. The blade includes a first, second and third edge. The first edge is sharpened to form a first cutting edge. The second edge is sharpened to form a second cutting edge and which is disposed on a side of the blade which is opposite to the first edge. The third edge is disposed on a side of the blade which is opposite to the shank and which is dull. The third edge extends between the first edge and the second edge in a single plane which is substantially perpendicular to the longitudinal axis of the handle, whereby third edge defines a single straight line.

BRIEF DESCRIPTION OF THE FIGURES

The accompanying drawings, which are incorporated in and form a part of the specification, illustrate different embodiments of the present and, together with the description, serve to explain the principles of the invention.

In the Drawings.

DETAILED DESCRIPTION OF PREFERRED EMBODIMENTS

Figure 1:
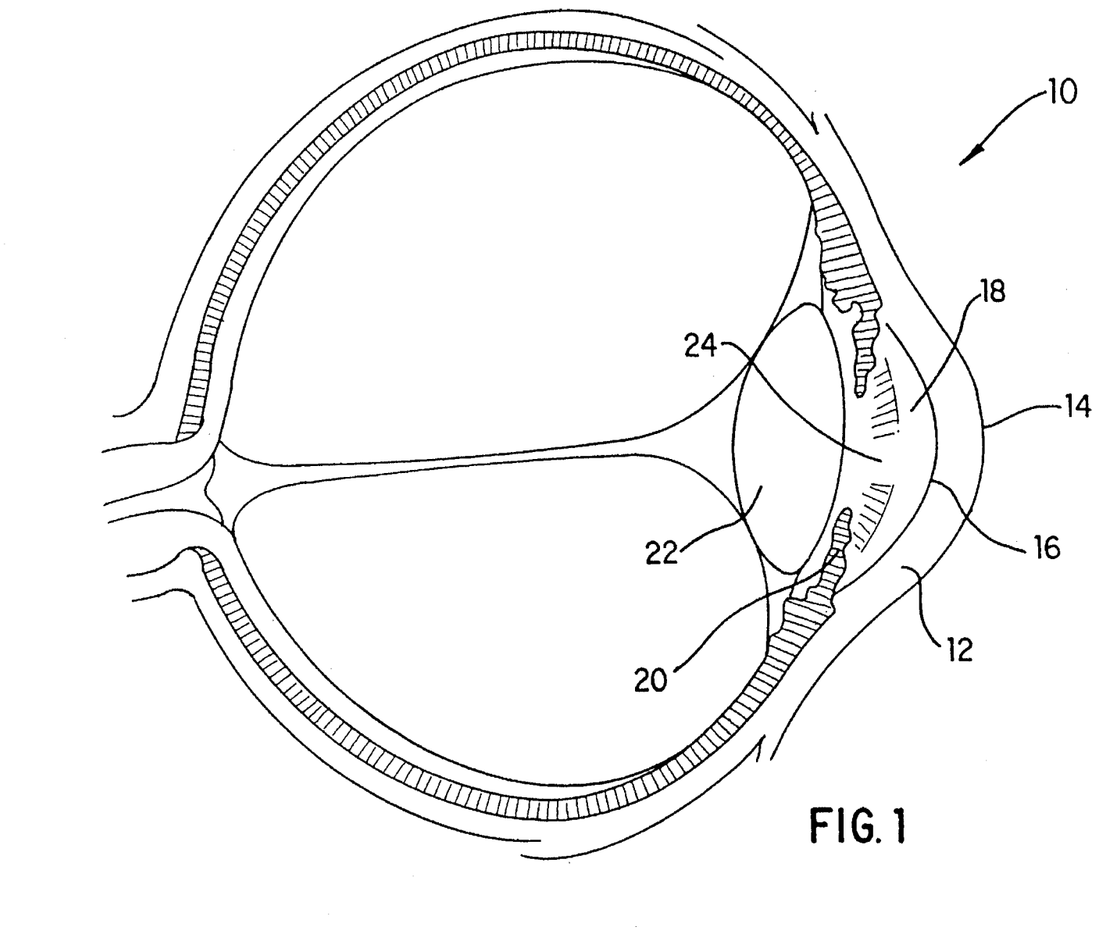
FIG. 1 is a cross sectional view taken through a human eye.

With reference to the drawing figures in which similar reference numbers are used to describe similar elements, a device is shown and discussed in the context of a surgical procedure on the cornea of an eye. It is understood that the invention may be used for other similar types of surgical procedures. Further, although a human eye is shown and described, the invention may be equally beneficial in surgery on the cornea of animals. Referring initially to FIG. 1, a cross section of a human eye is shown generally at 10. Eye 10 includes a cornea 12 having an exterior surface 14 and an interior surface 16. At exterior surface 14 of cornea 12 is the epithelium, which is a membrane that covers cornea 12. At interior surface 16 is the descemet membrane, which is a thin membrane that covers the back of cornea 12. Between the epithelium and descemet membrane is the stroma.

The thickness of the stroma of cornea 12 is measured by the distance between exterior surface 14 and interior surface 16. The thickness of cornea 12 varies radially from its central portion to its outer periphery. Specifically, cornea 12 is thinnest at its central portion and gradually becomes thicker when traveling radially outward toward the outer periphery. For example, the central portion of cornea 12 may have a thickness of 500 microns and the outer periphery of cornea 12 may have a thickness of 700 microns. For purposes of illustration, the variation in the thickness of cornea 12 is exaggerated in the figures. Behind cornea 12 is an anterior chamber 18, an iris 20, a lens 22 and a pupil 24.

As discussed above, surgical procedures to reduce myopia and astigmatism in an eye require surgery on cornea 12. In particular, a pattern of incisions are marked on the surface of cornea 12 by the use of an instrument, which creates a temporary, superficial depression or indentation in the surface of cornea 12 without cutting into cornea 12. Conventionally, an optical zone marker is employed to make a single circular mark on cornea 12 at an outer periphery of an optical zone of eye 10. The single circular mark is then used as a reference to indicate one end of incision 26. After marking cornea 12, the surgeon cuts incisions into cornea 12.

Figures 2, 3, 4, 5:
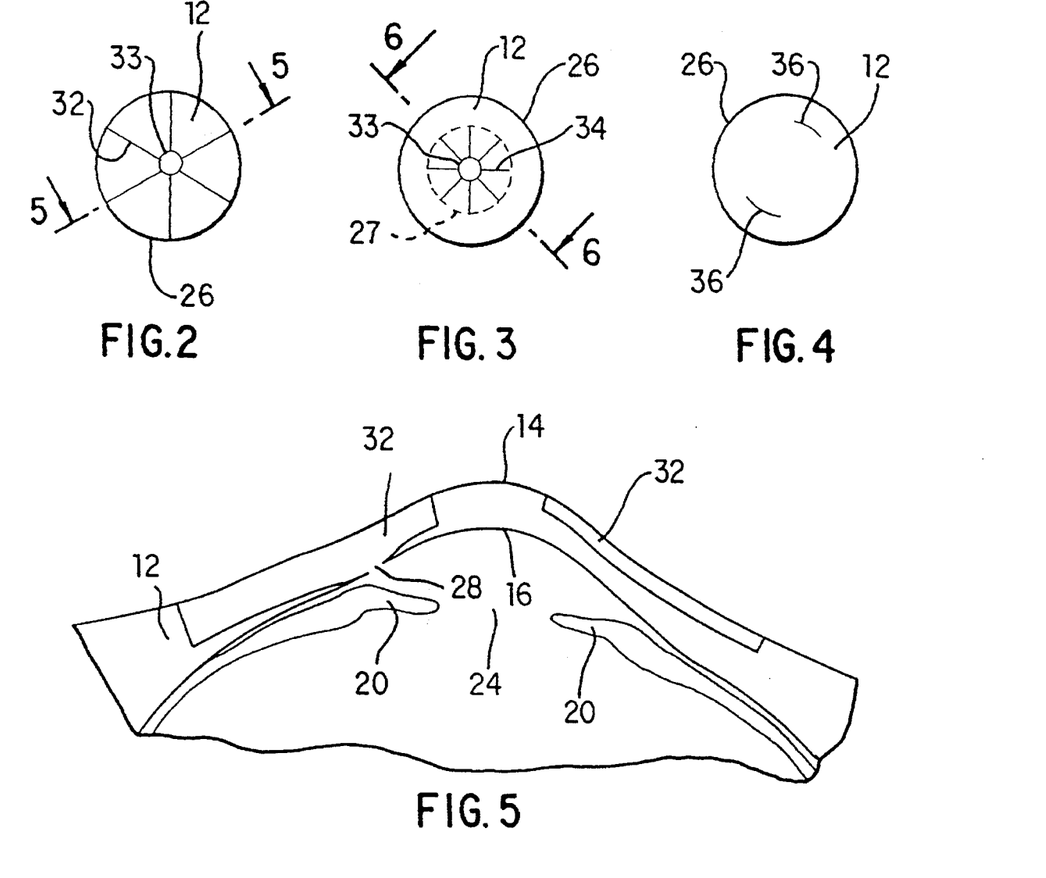
FIG. 2 shows a front view of an eye having a pattern of incisions cut into a cornea of the eye.
FIG. 3 shows a front view of an eye having a different pattern of incisions cut into the cornea of the eye.
FIG. 4 shows a front view of an eye having yet another pattern of incisions cut into the cornea of the eye.
FIG. 5 shows a cross section taken along line 5—5 shown in FIG. 2.

Referring now to FIGS. 2–4, different patterns which may be first marked and then cut into cornea 12 are shown. FIGS. 2 and 3 show patterns for surgery correcting myopia and FIG. 4 shows a pattern for surgery correcting astigmatism. Cornea 12 has an outer periphery 26, a paracentral portion 27 indicated generally by a broken line (FIG. 3) and a central portion 33 defining a clear central zone (ie. the incisions do not extend into this central portion 33) inside central zone 33. FIG. 2 shows the conventional pattern of four or more spoke-like full radial incisions 32 extending radially from central portion 33 in cornea 12. Full radial incisions 32 extend radially from central portion 33 to outer periphery 26 of cornea 12.

With the use of the present invention, a unique pattern of incisions is possible that causes less weakening of cornea 12, yet yields at least equivalent results as using full radial incisions. This is possible because of blade 48, and furthermore because of marking device 100. This pattern includes partial radial incisions 34, as shown in FIG. 3, which extend from central portion 33 to paracentral portion 27. This pattern is possible with the blade of the present invention, because partial radial incisions 34 can be made deeper and can be made more even at the bottom of the incision for almost the entire length of the incision than is currently possible. With this pattern of central radial incisions 34 it is possible to make the diameter of central portion 33 larger. By making central portion 33 larger, the clear central zone (without any cuts or incisions) is larger. Essentially, by having a larger diameter clear central zone, the incisions are spaced further from the optical zone of eye. Since glare is caused by light reflecting off the incisions in cornea 12 into the optical zone of the eye, increasing the clear central zone reduces glare. Although glare may not cause damage to eye 10, glare is distracting and a nuisance to keratotomy patients. With the use of the blade of the present invention, it also possible to increase the diameter of the clear central zone in other patterns of incisions, for example, the pattern shown in FIG. 2.

Another pattern of incisions made during surgery for correcting astigmatism is shown in FIG. 4. In this pattern, arcuate incisions 36 are cut into cornea 12 so as to be concentric with outer periphery 26 of cornea 12.

As discussed above, in procedures such as RK and AK, each incision should extend into at least 90% of the thickness of cornea 12 (from exterior surface 14 to interior surface 16), while not perforating cornea 12. As shown in FIG. 5, because the depth of full radial incision 32 cannot be precisely and reliably measured during surgery, they may be too deep or too shallow. For example, at the left side of FIG. 5, full radial incision 32 is shown to have been cut too deeply into cornea 12. As a result, cornea 12 has been perforated, as shown at 28. In contrast, on the right side of FIG. 5, another full radial incision 34 is shown which is too shallow (i.e., extends less than 50% into the thickness of cornea 12). This type of shallow incision occurs quite frequently with the use of the conventional sharp pointed tip diamond blade because the surgeon must be especially cautious not to perforate the cornea. When the surgeon attempts to deepen the incision with the sharp diamond blade more often than not, the sharp blade perforates cornea 12. In either instance, the results shown in FIG. 5 are undesirable.

Moreover, since the thickness of cornea 12 increases radially from the center of cornea 12 toward its outer periphery 26, it is especially difficult to obtain an incision that extends into nearly an entire thickness of cornea 12 over almost the entire length of the incision. This is especially difficult because the depth of an incision should preferably vary across cornea 12 to achieve an at least 90% penetration of the blade into the varying thickness cornea 12. In particular, incisions need to be deeper at outer periphery 26 where the cornea thickness is greater than at the center of cornea 12. When using a conventional sharp diamond blade having a pointed tip it is difficult to cut an even-bottomed varying depth thickness, while at the same time maintaining a smooth curvilinear bottom surface and avoiding perforation of cornea 12. Preferably, a bottom 37 of an incision should extend substantially parallel to interior surface 16 such that the uncut portion of the cornea adjacent to the incision has a substantially constant thickness of less than at least 90% of the thickness of cornea 12 along substantially the entire length of the incision.

Figure 6:
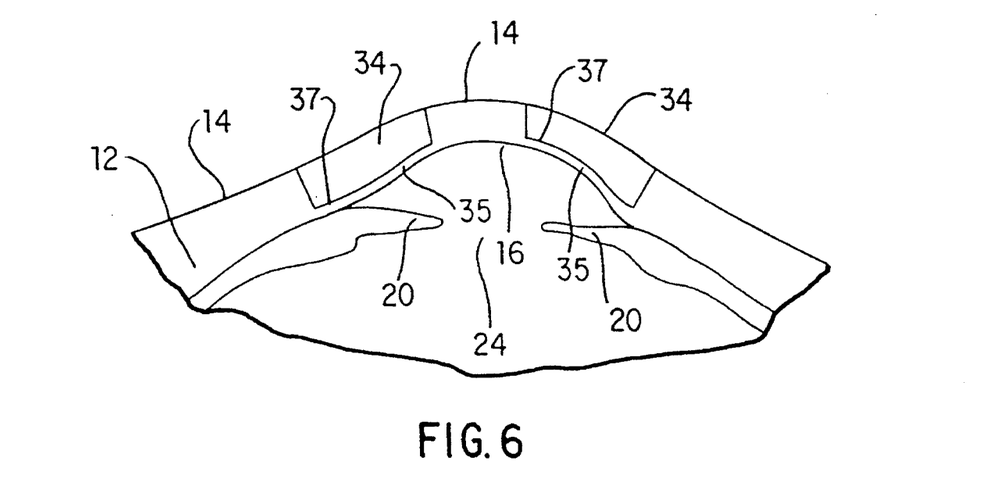
FIG. 6 shows a cross section taken along line 6—6 shown in FIG. 3.

FIG. 6 shows a successful surgical procedure in which incision 34 extends into cornea 12 from exterior surface 14 toward interior surface 16 at a depth just less than the full thickness of cornea 12. Moreover, this depth successfully accommodates the change in thickness of cornea 12 such that uncut portion 35 of cornea 12 has a substantially constant thickness along the main portion of the length of partial radial incision 34. In other words, the depth of incision 34 correspondingly varies with the changing depth of cornea 12 while deepening incision 34 to nearly an entire thickness of cornea 12 without fear of perforating the cornea. The device and method for obtaining the results of FIG. 6 are shown in FIGS. 7–11.

Before beginning keratotomy surgery, preferably, cornea 12 is marked. Cornea 12 can be marked by any conventional instruments. In the alternative, with the present invention, a novel marking device can be employed to mark the surface of cornea 12 and is shown generally at 100 in FIG. 7.

Figure 7:
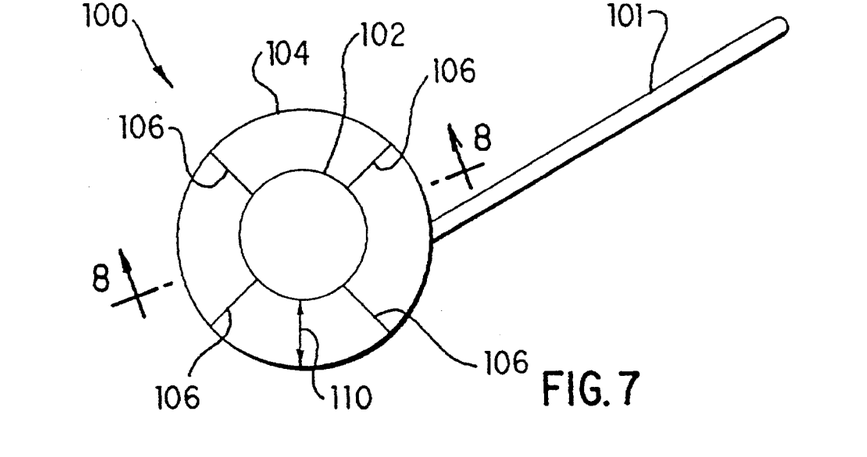
FIG. 7 shows a marking device in accordance with the present invention.

Marking device 100 is employed to mark two concentric substantially circular marks that serve as guides for the surgeon performing the surgery. Although discussed in detail below in the discussion of the method of the present invention, the two concentric marks serve as boundaries for cutting and enhancing incisions 32. For example, in one embodiment, the two concentric marks serve as the outer boundaries for the maximum length of the radial incisions 34. In another embodiment, one of the marks serves as a guide for cutting incisions 34 and the other mark serves as a guide for enhancing incisions 34.

Marking device 100 is preferably made of surgical steel for example. Marking device 100 includes a handle 101 attached at one end to an outer marker 104. Handle 101 extends outwardly at an angle from outer marker 104 and is attached by conventional means such as welding. Spaced radially inward from outer marker 104 is a central marker 102. Central and outer markers 102 and 104 are circular cylindrically shaped rings made of a thin sheet of surgical steel, for example, and have dull edges so that when marking cornea 12, a depression is made in cornea 12 without cutting cornea 12.

Figure 8:
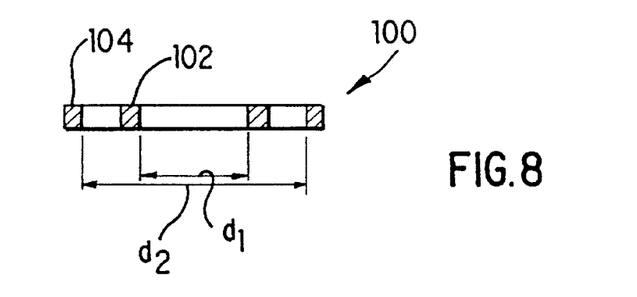
FIG. 8 shows a cross section taken along line 8—8 shown in FIG. 7.

Central marker 102 is connected to outer marker 104 by supports 106 extending radially between central and outer markers 102 and 104. Supports 106 may be employed to mark the placement of the radially extending incisions 34. Central marker 102, outer marker 104, and supports 106 can be monolithic or connected together by welding. As an alternative, the entire marking device 100 may be molded as a single unit through the use of any conventional molding processes. FIG. 8 shows a cross section taken through central and outer marks 102 and 104 of marking device 100.

Central and outer markers 102 and 104 define a space therebetween which marks the outermost ends of a maximum length of incision 34 in cornea 12. The radial distance between central marker 102 and outer marker 104 is shown generally by reference numeral 110.

In use, central marker 102 is positioned over central portions 33 of cornea 12. By applying pressure to marking device 100, two concentric marks are formed on cornea 12. Radial incisions 34 may also be marked at this time. Once cornea 12 has been marked, cornea 12 can be cut.

As shown in FIG. 8, central marker 102 has a first diameter $d_1$, and outer marker 104 has a second diameter $d_2$. These dimensions, namely, diameters $d_1$ and $d_2$, may differ and are determined based on, for example, the degree of myopia and the age of the patient. However, diameters $d_1$ and $d_2$ are related to each other.

The following provides examples of sets of diameters $d_1$ and $d_2$ for central and outer markers 102 and 104 for sample marking devices, which accommodate varying degrees of myopia and ages of patients.

TABLE I

| Diameter $d_1$ of Central Marker 102 | Diameter of $d_2$ of Outer Marker 104 |
| --- | --- |
| 3.00 | 5.0 |
| 3.25 | 5.0 |
| 3.50 | 5.0 |
| 4.00 | 5.0 |
| 4.25 | 5.0 |
| 4.50 | 5.0 |

TABLE II

| Diameter $d_1$ of Central Marker 102 | Diameter of $d_2$ of Outer Marker 104 |
| --- | --- |
| 3.00 | 4.5 |
| 3.25 | 4.5 |
| 3.50 | 4.5 |
| 4.00 | 4.5 |
| 4.25 | 4.5 |

Figure 9:
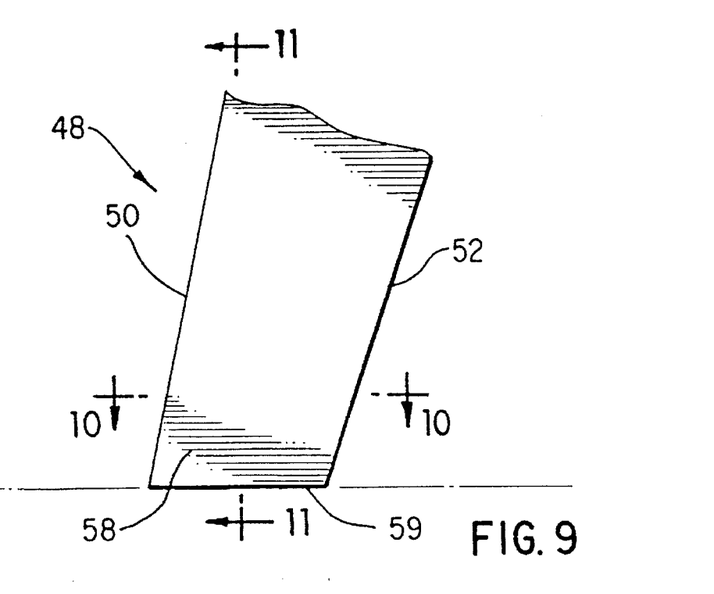
FIG. 9 shows a blade in accordance with the present invention.

The present invention also relates to a blade shown generally at 48 in FIG. 9. Blade 48 comprises a generally flat piece of material. Blade 48 preferably is made of diamond, although materials such as precious stone, semiprecious stone, cubic zirconium, artificial stone, synthetic stone and surgical steel may also be used. Blade 48 has two substantially parallel sides, generally opposed to each other, and forming a first edge 50 and a second edge 52. Distal end 58 of blade 48 has a third edge 59 that extends between first edge 50 and second edge 52. Third edge 59 lies in a single plane along its entire length between first edge 50 and second edge 52. Accordingly, a single straight linear third edge 59 is obtained which offers numerous advantages over blades having nonlinear distal edges, as will be discussed below. Since third edge 59 is fairly broad, third edge 59 offers a stable base or support to keep blade 48 from tilting during surgery. If blade 48 has a tendency to tilt during surgery, the corners of blade 48 may risk perforating the cornea. First edge 50 and second edge 52 are substantially planar and join distal end 58 at approximately a 90° angle. Although first and second edges 50 and 52 are each shown to be substantially linear, it is within the scope of the invention to have, for example, second edge 52 non-linear such that a first portion of second edge 52 is disposed at a first angle and a second edge 52 is disposed at a second angle different from the first angle. Distal end 58 is disposed opposite to a shank of blade 48, which is attachable to a handle, as will be discussed in detail below.

Figure 10:
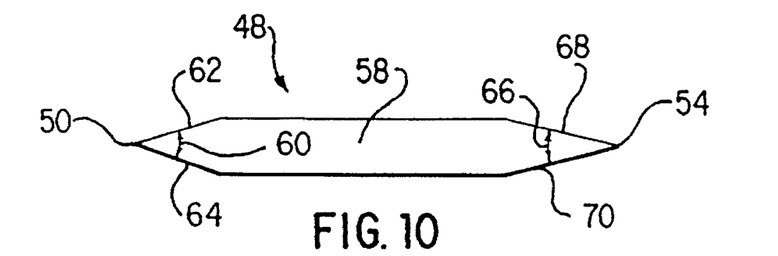
FIG. 10 shows a cross section taken along line 10—10 shown in FIG. 9.
Figure 11:
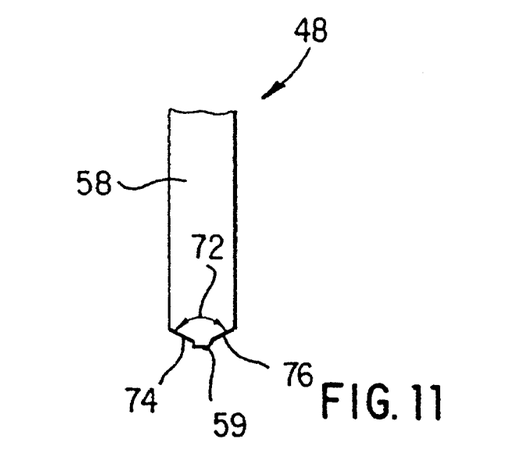
FIG. 11 shows a cross section taken along line 11—11 shown in FIG. 9.

As shown in FIG. 10, first edge 50 and second edge 52 are shaped, for example, by sharpening, to form a first cutting edge and a second cutting edge, respectively, which are sharp. In particular, a first angle 60 is defined by sloping sides 62 and 64 of first edge 50. A second angle 66 is defined by sloping sides 68 and 70 on lower portion 54 of second edge 52. Preferably, first and second angles 60 and 66 are 35° or less. Referring now to FIG. 11, third edge 59 of distal end 58 is dull. In particular, a third angle 72 is defined by sloping sides 74 and 76 of distal end 58. Preferably, third angle 72 is equal to or greater than 110°. As a result, first edge 50 and second edge 52 of blade 48 are sharp, while third edge 59 of distal end 58 is dull. However, it is within the scope of the invention to have second edge 52 entirely or partially dull.

Figure 12:
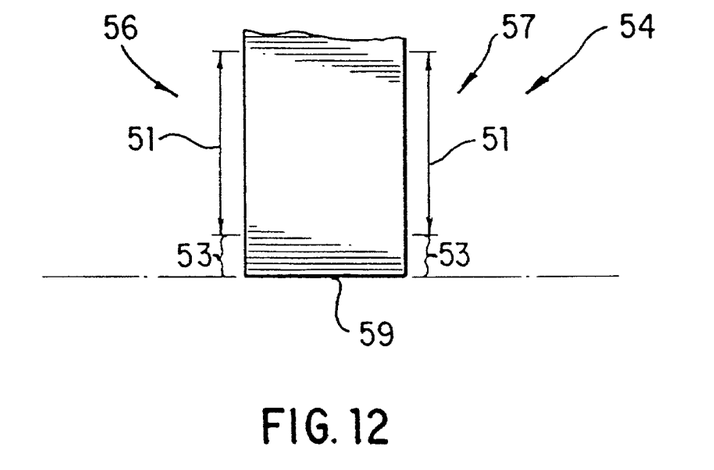
FIG. 12 shows another embodiment of the blade in accordance with the present invention.

In an alternative embodiment, shown in FIG. 12, a blade 54 is shown having dull tip 59, as discussed above. First and second edges 56 and 57 of blade 54 are of a hybrid construction. In particular, a first portion 53 on each of first and second edges 56 and 57 adjacent dull tip 59 is dull. In particular, first portion 53 extends approximately 50 microns along each of first and second edges 56 and 57 from dull tip 59 toward the shank of blade 54. A second portion 51 on each of first and second edges 56 and 57 extends along a same plane as and from first portion 53 toward the shank of blade 54. With this hybrid blade 54 it is possible to further improve the safety associated with cutting an incision in cornea 12 by eliminating any sharpness in the vicinity of the bottom of the incision, yet since second portions 51 are sharp, hybrid blade 54 is capable of cutting. In particular, if hybrid blade 54 is tilted, since first portion 53 of first and second edges 56 and 57 are dull, the risk of perforating cornea 12 is significantly reduced.

Figures 13, 14:
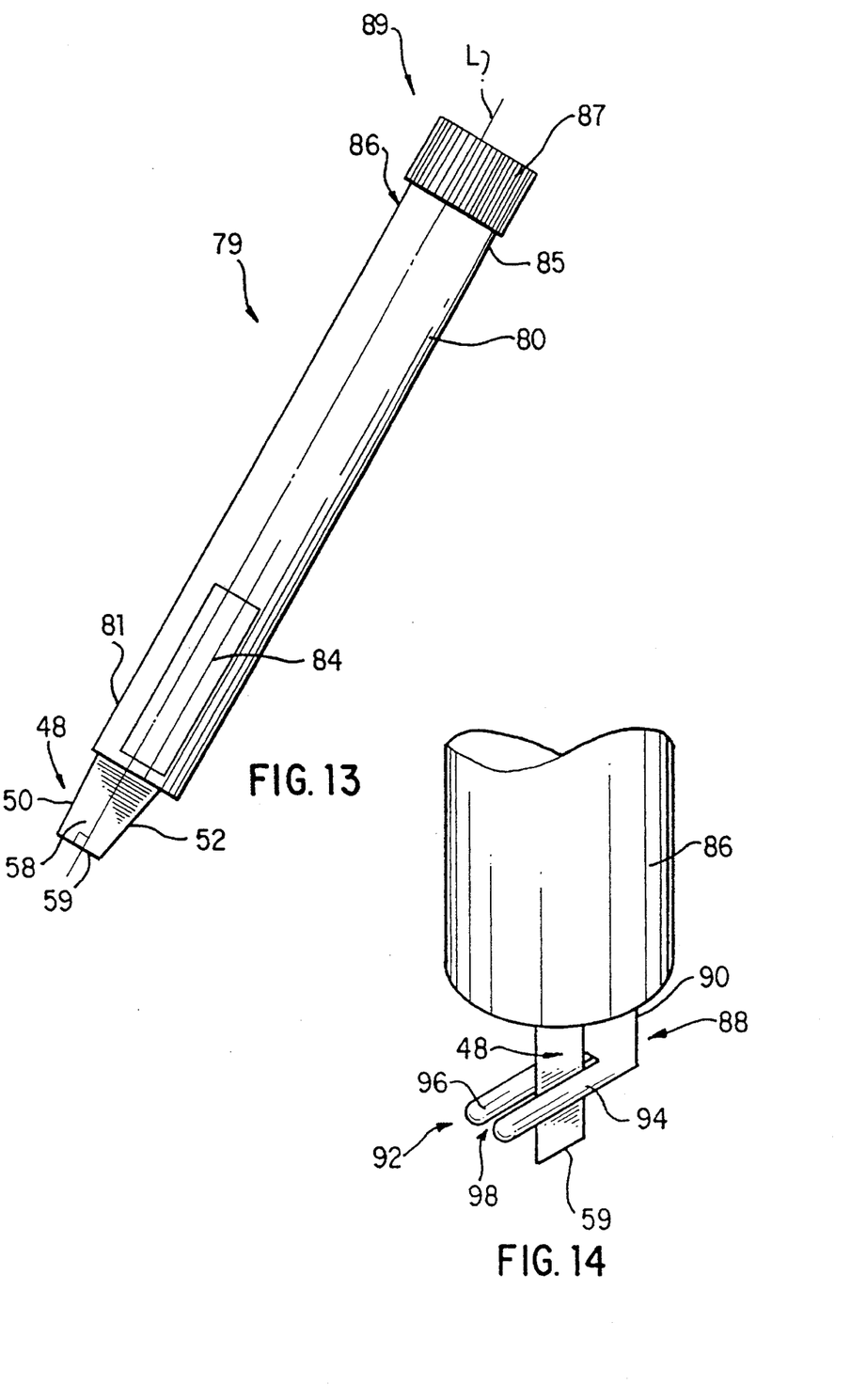
FIG. 13 shows a knife of the present invention including a handpiece, a blade and a micrometer control for the blade.
FIG. 14 shows another embodiment of the knife of the present invention having a handpiece with a footplate.

Referring now to FIG. 13, a handpiece utilizing the blade of the present invention is shown generally at 79. Handpiece 79 has a generally longitudinal axis L. Handpiece 79 includes a handle 80 and a blade 48 as discussed above. Handle 80 slidably receives blade 48 through end 81. The shank of blade 48 is disposed in handle 80. Handpiece 79 may include a micrometer control, shown generally at 89, blade 48 is slidable along longitudinal axis L of handle 80 so as to be extended from and be retracted into handle 80. The micrometer control includes a twist cap 87 that when rotated in one direction of rotation, extends blade 48 outwardly from handle 80, and when rotated in an opposite direction, retracts blade 48 into handle 80. To measure or track the amount of movement of blade 48, markings 89 are provided longitudinally on end 85 of handle 80. The unit of measure for markings 89 is preferably micrometers. The micrometer control of the present invention is similar to the type of micrometer control disclosed is U.S. Pat. No. 4,884,569 to Fedorov et al., the entire disclosure of which is incorporated herein by reference.

Handle 80 may be made of any conventional material used in surgical environments such as titaniumor stainless steel. In addition, handle 80 may be weighted to reduce the amount of pressure or force that needs to be exerted by the surgeon during surgery to deepen the incision. To weight handle 80, a weight 84 may be used or handle 80 may be weighted inherently by the type of material used to make the handle.

Handpiece 86 may also include a footplate holder 88 as shown in FIG. 14. Footplate holder 88 has a shank end 90 attached to handpiece 86, and a distal end, shown generally at 92, which is bifurcated into two footplates 94 and 96. Shank end 90 and footplates 94 and 96 of distal end 92 extend substantially perpendicular to each other. First footplate 94 and second footplate 96 are separated by an opening shown generally at 98. At least the lower flat sides of first footplate 94 and Second footplate 96 lie in a common plane. Footplate holder 88 is disposed on handpiece 86 such that blade 48 passes between first and second footplates 94 and 96 and through opening 98. Third edge 59 of blade 48 is disposed parallel to the common plane of first and second footplates 94 and 96. Footplate holder 88 may be mounted on handpiece 86 by any conventional means. First and second footplates 94 and 96 are designed to slide along exterior surface 14 of cornea 12. The location of first and second footplates 94 and 96 relative to third edge 59 of blade 48 can be adjusted by micrometer 89 to control the depth of the incision. Preferably, first and second footplates 94 and 96 are made of a clear or transparent material such as clear plastic so that a preexisting incision in the cornea is not blocked from the view of the surgeon. Instead, a surgeon can view the preexisting incision through first and second footplates 94 and 96.

The blade of this invention can be used at the time of the initial surgery or post-operatively to enhance an incision made by a conventional surgical method. Accordingly, in use, blade 48 of the present invention may be used in combination with conventional corneal surgical tools and techniques. In a preferred method of use at the time of initial surgery, after marking the cornea with the pattern of incisions for the type of surgery being performed, a corneal pachymetry is taken at central portion 33 of cornea 12 and at periphery 26 of cornea 12 to measure the thickness of the cornea at these points. The micrometer control is set to measure the desired depth of the cut into cornea 12. Then, the desired incisions are cut into cornea 12 using a conventional knife having a diamond blade with sharp edges and a pointed tip. The quantity and pattern of incisions will vary depending upon the surgery being performed and may include, for example, 4, 8 or 16 incisions. In the present invention, the conventional knife is used to create an initial incision that extends into amount of the corneas that is equal to 90% of the thickness of the central cornea, or more preferably, extends a depth equal to the central corneal depth, for example, 500 microns. Once these initial incisions are created with the conventional knife, then blade 48 of the present invention is used to complete the surgical procedure. That is, blade 48 is disposed in the existing corneal incision. By using very little or no hand pressure, the incision is deepened by sliding or moving blade 48, and more particularly, third dull edge 59 along or across the base of the incision or along the descements membrane while sharp edge 50 and sharp lower portion 54 cut or deepen the incision to nearly the entire thickness of cornea 12. However, because blade 48 has a dull and entirely linear or planar edge, there is no fear of perforating cornea 12. Moreover, an even-bottomed incision is made.

In the alternative, blade 48 is inserted into the cornea of the eye. An incision is created in the cornea of the eye which is almost the entire thickness of the cornea without perforating the cornea by moving the sharp edge of the blade along the cornea. The dull edge is moved along the descements membrane of the cornea while creating the incision. Again, since third edge 59 is linear across its entire length, it can serve as a guide during use, thereby enabling the surgeon to reliably deepen the incision and straighten out any unevenness at the base of the incision. In addition, since edge 59 is dull as well as completely linear, blade 48 can be used by a surgeon with confidence and without fear of accidentally perforating cornea 12 with distal end 58 of blade 48.

In addition, in the embodiment of the invention using weighted handle 80, since the third edge 59 of blade 48 is dull and linear, when the weighted handle 80 presses third edge 59 against the bottom of the incision, third edge 59 will not cut the incision because not only is third edge 59 dull, but it is linear thereby distributing the downward force across its entire surface. Whereas, if third edge 59 were a point, the weight would be distributed on a single point and likely puncture cornea 12. Accordingly, the surgeon does not have to exert pressure when deepening the incision, instead the surgeon only needs to concentrate on guiding blade 48 along the length of the incision to deepening the incision by cutting with sharp edge 50 and sharp lower portion 54 of blade 48.

In the alternative, blade 48 may be used in enhancement surgery where preexisting incisions were made during a previous surgery. Since the preexisting incisions remain accessible for reentry, blade 48 is simply disposed in the preexisting incisions for correcting or improving the cut or depth of the preexisting incision. For example, blade 48 can be used to smooth out the unevenness of the bottom of a preexisting incision and/or deepen the incision to almost an entire thickness of cornea 12.

Moreover, as discussed above, in accordance with the present invention, incisions cut by blade 48 into cornea 12 consistently cut at least 90% of cornea 12 for almost the entire length of the incision. Therefore, with the present invention, it is possible to make shorter incisions, for example, partial radial incisions 34 as shown in FIG. 3. This procedure may be referred to as mini RK surgery. Mini RK surgery causes less weakening of the cornea than conventional RK as shown in FIG. 2. With mini RK surgery, the cornea is marked using marking device 100 to define the length of radial incisions 34. For example, the marker may include a 3.08 millimeter diameter central zone and 2.5 millimeter long radial markers. As discussed above, with mini RK surgery, weakening of cornea 12 and glare are reduced.

In another aspect of the invention, a kit is provided for use in a surgical procedure on a cornea of an eye. The kit includes marking device 100 and handpiece 89, for example. Marking device 100, as discussed above, is for marking cornea 12 of eye 10 with a pattern of marks. Handpiece 89 includes handle 80 with blade 48 of the present invention mounted thereon. A conventional diamond blade knife may also be included in this kit.

In yet another aspect of the invention, a method is provided for performing a surgical procedure on the cornea of an eye. The method includes measuring the thickness of the cornea using conventional tools mentioned above. A blade of the present invention that has a sharp edge and a dull edge is inserted into the cornea of the eye. An incision is created in the cornea of the eye which is almost the entire thickness of the cornea without perforating the cornea. This incision is created by moving the sharp edge of the blade along the cornea and moving the dull edge of the blade along the descements membrane of the cornea while creating the incision.

In another aspect of the invention, the method for performing a surgical procedure on the cornea of an eye may incorporate the use of a conventional blade. In particular, after the cornea is measured, an incision is cut in the cornea that is equal to approximately 90% of the thickness of the central cornea using a first blade having sharp edges and a pointed tip. The depth of the incision is enhanced by disposing the blade of the present invention, set at the depth of the peripheral cornea, in the incision. The dull edge on the distal end of the blade of the present invention is moved along the base of the incision such that the cornea is cut with the sharp edge of the blade of the present invention to enhance the depth of the incision. By doing so, the incision is deepened to almost the entire thickness of the cornea consistently and evenly across almost an entire length of the incision without perforating the cornea.

The method of the present invention may also incorporate the use of the marking device of the present invention. In particular, the marking device is used to mark the surface of the cornea with a first mark having a first diameter and a second mark concentric with the first mark having a second diameter greater than the first diameter. When partial radial incisions are to be cut in the cornea (mini RK pattern of incisions shown in FIG. 3), the first and second marks define a maximum length of the incision. In the alternative, when the conventional RK incisions are to be cut in the cornea (conventional pattern of incisions shown in FIG. 2), the marks serve two different purposes. In particular, the initial incision cut by the conventional knife is cut extending between the outer periphery of the eye and the first mark. Then, a portion of this initial incision that extends between the outer periphery of the eye and the second mark is enhanced using the blade of the present invention. It is only necessary to enhance the portion of the incision closer to the periphery and further from the central portion of the eye because the cornea of the eye becomes thicker moving toward the periphery and it is more difficult to cut the incision of the desired thickness and precision. In addition, by enhancing this initial incision in accordance with the method of the invention, it is possible to make the central zone of the cornea larger in diameter, which reduces the glare to the patient, as discussed above.

A preferred embodiment of the present invention was chosen and described in order to be best explain the principles of the present invention and its practical application to thereby enable others skilled in the art to best utilize the invention and various embodiments and with various modifications as are suited to the particular use contemplated. It is intended that the scope of the invention be defined by the claims appended hereto.

What is claimed is:

1. A surgical instrument, comprising:
   a handle having a longitudinal axis;
   a blade having a shank attached to said handle, said blade having:
   (a) a first edge which is sharpened to form a first cutting edge;
   (b) a second edge which is disposed on a side of said blade which is opposite to said first edge, said second edge having a first portion and a second portion extending along a same plane as said first portion, wherein said first portion is dull and said second portion is sharpened to form a second cutting edge; and
   (c) a third edge disposed on a side of said blade which is opposite to said shank and which is dull, wherein said third edge extends from said first edge to said first portion of said second edge in a single plane which is substantially perpendicular to said longitudinal axis of said handle, whereby said third edge defines a single straight line.

2. A surgical instrument according to claim 1, wherein said first and said second edges are planar.

3. A surgical instrument according to claim 1, wherein said second edge is non-planar.

4. A surgical instrument according to claim 3, wherein a portion of said second edge is dull.

5. A surgical instrument according to claim 1, wherein said first and second edges each have a first portion adjacent said third edge which is dull and a second portion adjacent said shank that is sharpened to form a second portion cutting edge and said first portion is substantially 50 microns in length.

6. A surgical instrument according to claim 1, wherein said third edge is formed by a first and a second sloping side which define an angle therebetween which is equal to or greater than 110°.

7. A surgical instrument according to claim 1, wherein said first edge is formed by a third and a fourth sloping side which define an angle therebetween which is equal to or less than 35°.

8. A surgical instrument according to claim 1, wherein said second edge is formed by a fifth and sixth sloping side which define an angle therebetween which is equal to or less than 35°.

9. A surgical instrument according to claim 1, wherein said blade is made of a material selected from the group consisting of precious stone, semiprecious stone, artificial stone, surgical steel, diamond, cubic zirconium and surgical steel.

10. A surgical instrument according to claim 1, wherein said handle is weighted.

11. A surgical instrument according to claim 1, further comprising:
    a footplate attached to said handle, wherein said footplate is made of a transparent material.

12. A surgical instrument according to claim 1, further comprising:
    a footplate holder attached to said handle, wherein said footplate holder includes a shank end attached to said handpiece and a second end which is bifurcated to form a first footplate and a second footplate, said second end extending in a common plane and defining an opening therebetween, wherein said blade is disposed in said opening and wherein said single plane defined by said third edge of said blade is parallel to said common plane defined by said first and second footplates.

13. A surgical instrument accordingly to claim 12, wherein said first and second footplates are made of a transparent material.

14. A method for performing a surgical procedure on the cornea of an eye, comprising the steps of:
    measuring the thickness of the cornea;
    inserting the blade of a surgical instrument into the cornea of the eye, wherein a shank of said blade is attached to a handle of said surgical instrument, said handle having a longitudinal axis and said blade having,
    (a) a first edge which is sharpened to form a first cutting edge,
    (b) a second edge which is disposed on a side of said blade which is opposite to said first edge, said second edge having a first portion and a second portion extending along a same plane as said first portion, wherein said first portion is dull and said second portion is sharpened to form a second cutting edge, and
    (c) a third edge disposed on a side of said blade which is opposite to said shank and which is dull, wherein said third edge extends from said first edge to said first portion of said second edge in a single plane which is substantially perpendicular to said longitudinal axis of said handle, whereby said third edge defines a single straight line;
    creating an incision in the cornea of the eye which is almost the entire thickness of the cornea without perthrating the cornea by moving one of said first and second sharp edges of said blade along the cornea; and
    moving said third edge along the descements membrane of said cornea while creating the incision.

15. A method according to claim 14, wherein said step of cutting said incision comprises the step of cutting a partial radial incision in said cornea.

16. A method for performing a surgical procedure on the cornea of an eye, comprising the steps of:
    measuring the cornea;
    cutting an incision in the cornea that is equal to approximately 90% of the thickness of the central cornea using a first blade having a sharp edge and a pointed tip;
    enhancing the depth of said incision by using a surgical instrument having a handle with a longitudinal axis and a second blade having a shank attached to said handle and by disposing said second blade in said incision to a depth substantially equal to a depth of the peripheral cornea, wherein the second blade has,
    (a) a first edge which is sharpened to form a first cutting edge,
    (b) a second edge which is disposed on a side of said second blade which is opposite to said first edge, said second edge having a first portion and a second portion extending along a same plane as said first portion, wherein said first portion is dull and said second portion is sharpened to form a second cutting edge, and (c) a third edge disposed on a side of said second blade which is opposite to said shank and which is dull, wherein said third edge extends from said first edge to said first portion of said second edge in a single plane which is substantially perpendicular to said longitudinal axis of said handle, whereby said third edge defines a single straight line, whereby said third edge of said second blade is moved along the base of said incision and at least one of said first edge and said second portion of said second edge cuts said cornea to enhance the depth of said incision; and deepening said incision to almost the entire thickness of said cornea consistently and evenly across almost an entire length of said incision without perforating the cornea.

17. A method according to claim 16, wherein said step of cutting said incision comprises the step of cutting a partial radial incision in said cornea.

18. A method according to claim 16, after the step of measuring, further comprising the step of:

marking a surface of the cornea with a first mark with a first diameter and a second mark concentric with the first mark having a second diameter greater than the first diameter, wherein the first and second marks define a maximum length of the incision.

19. A method according to claim 18, further comprising the step of:

marking a surface of the cornea with a first mark with a first diameter and a second mark concentric with the first mark having a second diameter greater than the first diameter, wherein the initial incision is cut extending between an outer periphery of the eye and the first mark, and wherein a portion of the initial incision extending between the outer periphery of the eye and the second mark is enhanced with the second blade.

* * * * *